(12) United States Patent
Teodorescu (10) Patent No.: US 10,633,941 B2
(45) Date of Patent: Apr. 28, 2020

(54) SHAKER CONTROL AND OPTIMIZATION

(71) Applicant: Halliburton Energy Services, Inc., Houston, TX (US)

(72) Inventor: Gabriel Teodorescu, The Woodlands, TX (US)

(73) Assignee: Halliburton Energy Services, Inc., Houston, TX (US)

( * ) Notice: Subject to any disclaimer, the term of this patent is extended or adjusted under 35 U.S.C. 154(b) by 123 days.

(21) Appl. No.: 14/900,407

(22) PCT Filed: Apr. 20, 2015

(86) PCT No.: PCT/US2015/026661
§ 371 (c)(1),
(2) Date: Dec. 21, 2015

(87) PCT Pub. No.: WO2016/171650
PCT Pub. Date: Oct. 27, 2016

(65) Prior Publication Data
US 2017/0089153 A1  Mar. 30, 2017

(51) Int. Cl.
*B01D 33/03* (2006.01)
*E21B 21/06* (2006.01)
(Continued)

(52) U.S. Cl.
CPC ........ *E21B 21/065* (2013.01); *B01D 33/0376* (2013.01); *E21B 21/01* (2013.01);
(Continued)

(58) Field of Classification Search
CPC .......................... B01D 33/0376; E21B 21/065
See application file for complete search history.

(56) References Cited

U.S. PATENT DOCUMENTS

| | | | |
|---|---|---|---|
| 4,809,791 A * | 3/1989 | Hayatdavoudi | .... B01D 33/0346 175/206 |
| 6,349,595 B1 | 2/2002 | Civolani et al. | |

(Continued)

FOREIGN PATENT DOCUMENTS

| | | |
|---|---|---|
| CA | 2857484 | 6/2013 |
| WO | 2014201457 | 12/2014 |

OTHER PUBLICATIONS

International Search Report and Written Opinion for PCT/US2015/026661 dated Nov. 26, 2015.
(Continued)

*Primary Examiner* — David J Bagnell
*Assistant Examiner* — Brandon M Duck
(74) *Attorney, Agent, or Firm* — Tenley Krueger; C. Tumey Law Group PLLC (57) ABSTRACT

Monitoring drill cuttings suspended within a drilling fluid with one or more cuttings detection devices as the drill cuttings traverse one or more shaker screens of a shaker. Drill cuttings data of the drill cuttings is then generated with the one or more cuttings detection devices. Analyzing and processing the drill cuttings data with one or more processors included in a data acquisition system and thereby generating processed drill cuttings data. The processed drill cuttings data is indicative of at least one of a cuttings size distribution and a density of the drill cuttings. One or more operational parameters of the shaker may then be modified based on the processed drill cuttings data.

21 Claims, 3 Drawing Sheets

(51) Int. Cl.
*G01N 33/24* (2006.01)
*E21B 21/01* (2006.01)
*E21B 43/10* (2006.01)
*G01N 15/02* (2006.01)
*G01N 15/00* (2006.01)

(52) U.S. Cl.
CPC ............ *E21B 21/06* (2013.01); *E21B 21/066* (2013.01); *E21B 43/10* (2013.01); *G01N 15/0227* (2013.01); *G01N 33/24* (2013.01); *G01N 2015/0053* (2013.01)

(56) References Cited

U.S. PATENT DOCUMENTS

| | | | |
|---|---|---|---|
| 8,575,541 | B1 | 11/2013 | Jamison et al. |
| 9,000,358 | B2 | 4/2015 | Jamison et al. |
| 2006/0243643 | A1* | 11/2006 | Scott .................. B01D 33/0376 209/309 |
| 2010/0135536 | A1* | 6/2010 | Dvorkin ............... G01N 23/046 382/109 |
| 2010/0312370 | A1* | 12/2010 | Lind ....................... E21B 41/00 700/98 |
| 2011/0109755 | A1* | 5/2011 | Joshi .................. H04N 5/23248 348/208.5 |
| 2014/0046628 | A1 | 2/2014 | Ligneul et al. |
| 2014/0172177 | A1 | 6/2014 | Jamison et al. |
| 2014/0214325 | A1 | 7/2014 | Wessling et al. |
| 2014/0278111 | A1* | 9/2014 | Gerrie ................. E21B 47/0002 702/8 |
| 2014/0333754 | A1* | 11/2014 | Graves .................... E21B 44/00 348/85 |
| 2016/0090799 | A1* | 3/2016 | Geehan ................. E21B 21/065 210/740 |
| 2017/0191919 | A1* | 7/2017 | Kulkarni ................ E21B 21/06 |

OTHER PUBLICATIONS

Canadian Examination Report for Application No. 2,978,060 dated Sep. 19, 2018.
Canadian Examination Report for Application No. 2,978,060 dated Jul. 22, 2019.

* cited by examiner

SHAKER CONTROL AND OPTIMIZATION

This application is the national stage application of PCT/US2015/026661 by Gabriel Teodorescu, filed on Apr. 20, 2015, entitled Shaker Control and Optimization.

BACKGROUND

During the drilling of a hydrocarbon-producing well, a drilling fluid or "mud" is continuously circulated from a surface location down to the bottom of the wellbore being drilled and back to the surface again. The returning mud includes drill cuttings derived primarily from the formation being penetrated by a drill bit. In the case of multilateral wells, the drill cuttings may also include metal drill cuttings generated from milling or drilling through casing walls to form a lateral wellbore. Some downhole operations can also include borehole reaming operations, which can result in a unique type of cuttings returning to surface.

As can be appreciated, increasing the effectiveness and efficiency of drilling operations can reduce the cost of drilling wells for oil and gas exploration and subsequent production. One way of determining drilling efficiency is to observe the characteristic features of drill cuttings returning to the surface during drilling operations.

BRIEF DESCRIPTION OF THE DRAWINGS

The following figures are included to illustrate certain aspects of the present disclosure, and should not be viewed as exclusive embodiments. The subject matter disclosed is capable of considerable modifications, alterations, combinations, and equivalents in form and function, without departing from the scope of this disclosure.

DETAILED DESCRIPTION

The present disclosure is related to wellbore drilling operations and, more particularly, to monitoring drilling fluid returns and adjusting operational parameters of solids-control equipment used to clean the wellbore cuttings suspended in the drilling fluid returns based on the density and/or cuttings size distribution of the wellbore cuttings.

The embodiments described herein improve the drilling fluid cleaning capability of solids control equipment used in wellbore drilling systems. The solids control equipment includes at least one shaker, and drill cuttings suspended within spend drilling fluid may be monitored with one or more cuttings detection devices as the drill cuttings traverse one or more shaker screens of the shaker. Drill cuttings data of the drill cuttings may then be generated and transmitted to a data acquisition system where the drill cuttings data is analyzed and processed using one or more processors included in the data acquisition system. Processed drill cuttings data may then be generated and may be indicative of at least one of a cuttings size distribution and a density of the drill cuttings traversing the shaker screens. Based on the processed drill cuttings data, one or more operational parameters of the shaker may be modified and otherwise altered. An automated control system, for example, may modify the configuration or operation of the shaker, such as by altering its inclination angle, the vibration amplitude and/or frequency, the screen size (i.e., mesh size) of the shaker screens, and other specific parameters related to the shaker.

Figure 1:
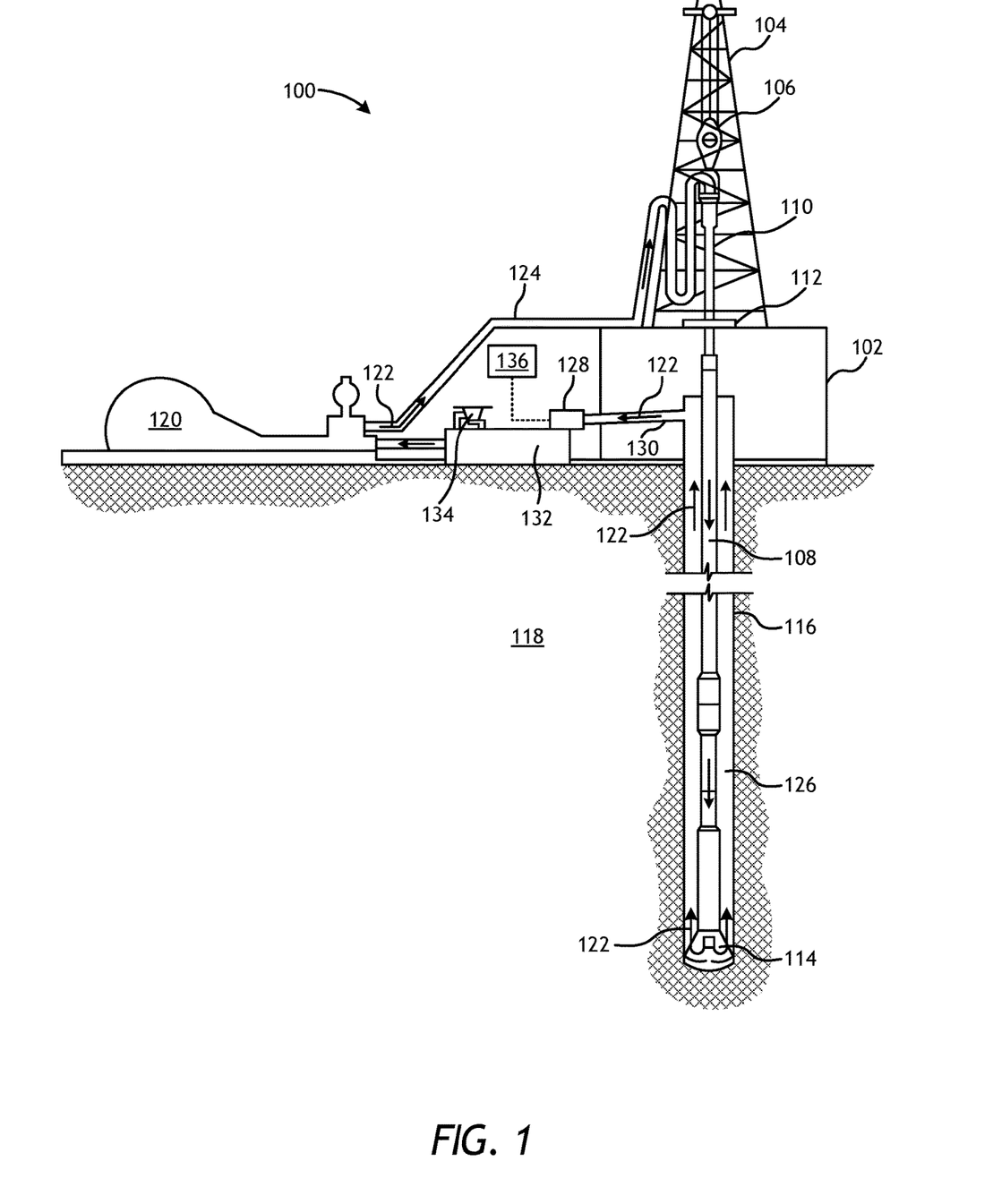
FIG. 1 is a schematic diagram of an exemplary drilling system that may employ the principles of the present disclosure.

Referring to FIG. 1, illustrated is an exemplary drilling system 100 that may employ the principles of the present disclosure, according to one or more embodiments. It should be noted that while FIG. 1 generally depicts a land-based drilling assembly, those skilled in the art will readily recognize that the principles described herein are equally applicable to subsea drilling operations that employ floating or sea-based platforms and rigs, without departing from the scope of the disclosure.

As illustrated, the drilling system 100 may include a drilling platform 102 that supports a derrick 104 having a traveling block 106 for raising and lowering a drill string 108. The drill string 108 may include, but is not limited to, drill pipe or coiled tubing, as generally known to those skilled in the art. A kelly 110 supports the drill string 108 as it is lowered through a rotary table 112. A drill bit 114 is attached to the distal end of the drill string 108 and is driven either by a downhole motor and/or via rotation of the drill string 108 by the rotary table 112. As the bit 114 rotates, it creates a borehole 116 that penetrates various subterranean formations 118.

A pump 120 (e.g., a mud pump) circulates drilling fluid 122 through a feed pipe 124 and to the kelly 110, which conveys the drilling fluid 122 downhole through the interior of the drill string 108 and through one or more orifices in the drill bit 114. The drilling fluid 122 is then circulated back to the surface via an annulus 126 defined between the drill string 108 and the walls of the borehole 116. At the surface, the recirculated or spent drilling fluid 122 exits the annulus 126 and may be conveyed to one or more fluid processing units, such as solids control equipment 128 via an interconnecting flow line 130.

The returning or spent drilling fluid 122 may contain cuttings and debris derived from the borehole 116 as the drill bit 114 grinds and scrapes the bottom and walls of the borehole 116. The spent drilling fluid 122 may also contain various solid additives, such as lost circulation materials, added to the drilling fluid 122 to enhance its operation. After passing through the fluid processing units, including the solids control equipment 128, a "cleaned" drilling fluid 122 may be deposited into a nearby retention pit 132 (i.e., a mud pit or suction tank). One or more chemicals, fluids, or additives may be added to the drilling fluid 122 via a mixing hopper 134 communicably coupled to or otherwise in fluid communication with the retention pit 132.

The solids control equipment 128 may be configured to substantially remove drill cuttings, solids, and other unwanted debris from the drilling fluid 122 and thereby separate waste from reusable particulates or materials. The solids control equipment 128 may include, but is not limited to, one or more of a shaker (e.g., shale shaker), a desilter, a desander, any combination thereof, and the like (typically solids separation units, based on particle size range). To remove drill cuttings and other unwanted solids from the returning drilling fluid 122, shakers used in the solids control equipment 128 may include one or more shaker screens (not shown) across which the drill cuttings may traverse to be separated from the drilling fluid 122.

A common problem encountered with solids control equipment 128 is the inefficient removal of unwanted solids and other particulates. For example, when solids control equipment 128, such as shakers, are not properly tuned, they can sometimes pass unwanted solids or other contaminating particulates into the retention pit 132, thereby providing a less effective drilling fluid 122 that is recirculated back into the borehole 116. In other cases, un-tuned solids control equipment 128 may inadvertently remove valuable additive components or materials from the drilling fluid 122, likewise having an adverse effect on the performance of the drilling fluid 122.

As will be appreciated, shaker screens used in the solids control equipment 128 must be able to handle the full circulation rate of the drilling fluid 122, thereby generating the bulk of drilling waste while simultaneously reclaiming the bulk of the drilling fluid 122. Shaker screens are typically the only equipment that is changed or altered to handle fluctuating deviations in drilling fluid 122 properties, such as changes in flow rate of the drilling fluid 122, or drilling conditions, such as the rate of penetration of the drill bit 114. Moreover, shaker screens are also typically the only equipment in conventional drilling systems that separate solids based on size.

According to embodiments of the present disclosure, the solids control equipment 128 and, more particularly, one or more shakers of the solids control equipment 128 may be communicably coupled to an imaging system 136 configured to help optimize operating parameters of the shakers. As described herein, the imaging system 136 may be configured to provide an operator with a real-time indication of the efficiency of the solids control equipment 128, thereby allowing the operator to proactively adjust and otherwise alter one or more operating parameters of the solids control equipment 128 (e.g., the shakers) to optimize its operation. Exemplary operating parameters of the solids control equipment 128 that may be adjusted may include, but are not limited to, increasing or decreasing an inclination angle (i.e., slope) of a shaker screen, increasing or decreasing a vibration amplitude of a shaker, increasing or decreasing a vibration frequency of a shaker, altering the size (i.e., mesh size) of a shaker screen, altering a configuration or mesh profile (e.g., alternative hole shapes) of a shaker screen, changing the operating speed (i.e., RPM) of a centrifuge, altering the frequency on variable speed drive (VSD) equipment), and any combination thereof.

In some embodiments, the imaging system 136 (photo, acoustic, inductive, capacitive etc.) may include or may otherwise be communicably coupled to an automated control system (not shown). When detection limits obtained by the imaging system 136 surpass a predetermined operational threshold for the drilling fluid 122, the automated control system may be configured to autonomously adjust the one or more operating parameters to bring operation back to suitable operational limits and otherwise optimize operation of the solids control equipment 128. As will be appreciated, fine-tuning the solids control equipment 128 will ensure that the drilling fluid 122 is maintained at proper and efficient operating levels. Moreover, when proper solids control practices are utilized, the cost to maintain the drilling fluid 122 and related equipment may decrease greatly.

Figure 2:
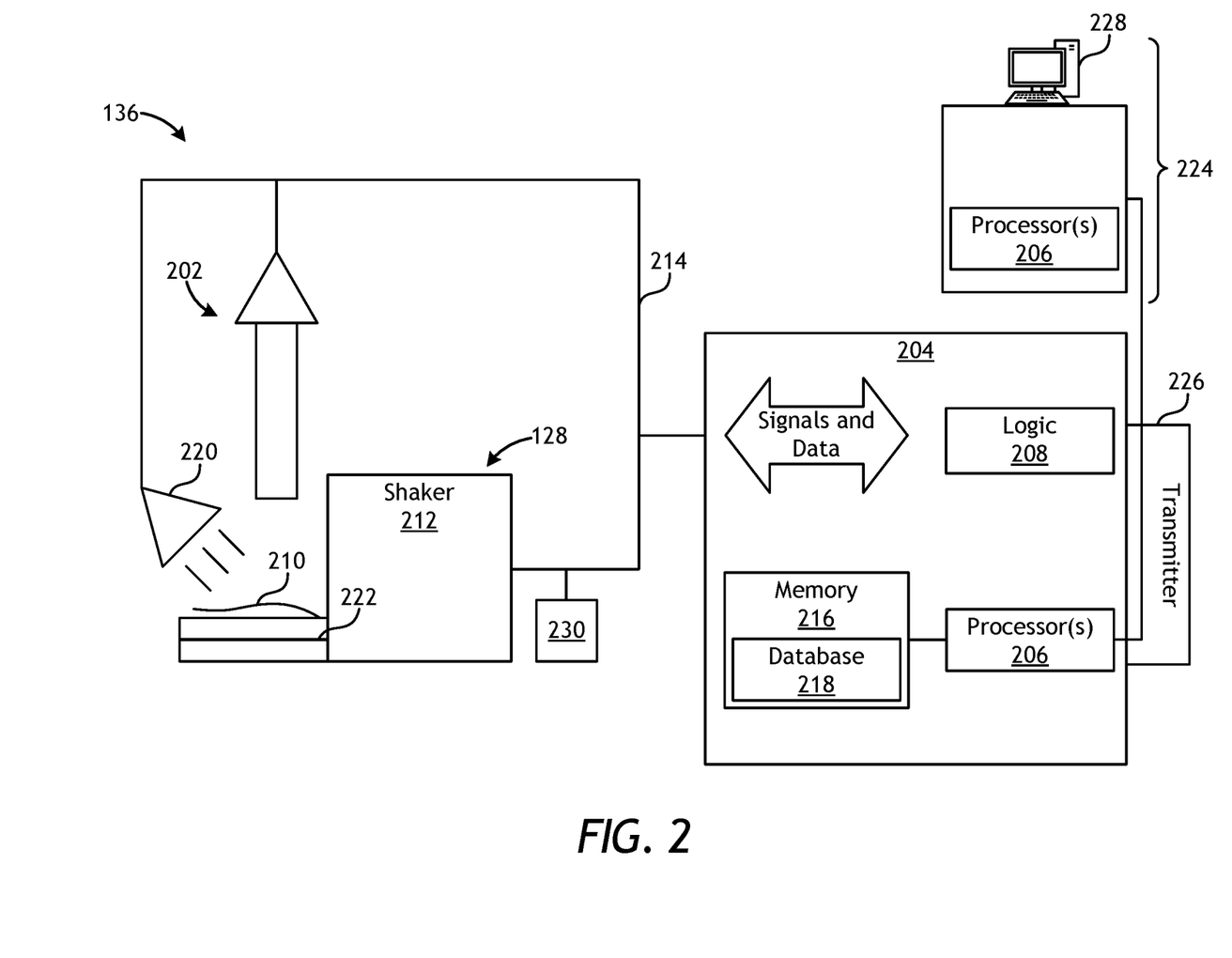
FIG. 2 is a schematic diagram of the imaging system of FIG. 1 used in carrying out the principles of the present disclosure.

Referring now to FIG. 2, with continued reference to FIG. 1, illustrated is a schematic diagram of the imaging system 136 of FIG. 1, according to one or more embodiments. It should be noted, however, that the imaging system 136 schematically depicted in FIG. 2 is only an example of one type of imaging system, device, or apparatus that may be used in keeping with the principles of the present disclosure. Indeed, other types and configurations of imaging systems that incorporate other computer design configurations may alternatively and suitably incorporate the principles of the present disclosure, without departing from the scope of the disclosure. Accordingly, the following description of the imaging system 136 is provided for illustrative purposes only and should not be considered limiting.

In some embodiments, the imaging system 136 may be located on or near the drilling platform 102 (FIG. 1). In other embodiments, however, any of the component parts or modules shown in FIG. 2 may be located at a remote location, without departing from the scope of the disclosure. For instance, some of the data and processing modules of the imaging system 136 may be located at a remote operation center, where the data could be received and analyzed by a geologist, a mud logger, or another type of logging professional. In addition, the remote location may comprise a mobile device, such as a tablet or handheld computer, and the data and/or resulting computational analysis may be transmitted via a data delivery system, such as Halliburton's INSITE ANYWHERE®, or via any other mobile transfer standard utilized in the industry.

As illustrated, the imaging system 136 may include one or more cuttings (or solids) detection devices 202 communicably coupled to and otherwise in communication with a data acquisition system 204. The cuttings detection device 202 (hereafter the "device 202") may be positioned adjacent the solids control equipment 128 and communicably coupled to the data acquisition system 204. The data acquisition system 204 may also be communicably coupled to the solids control equipment 128 and, in some embodiments, may be configured to provide commands thereto to optimize operation of the solids control equipment 128. The data acquisition system 204 may be communicably coupled to the device 202 and the solids control equipment 128 via any suitable telecommunication means (e.g., wired or wireless).

The data acquisition system 204 may include one or more processors 206 and logic 208, perhaps comprising a programmable data acquisition subsystem. The device 202 may be configured to monitor drill cuttings 210 as they move across one or more shakers 212 included in the solids control equipment 128, and the logic 208 may be used to acquire drill cuttings data 214 from the device 202 for processing. The data acquisition system 204 may further include a memory 216 communicably coupled to the processor(s) 206 and used to compile or store the acquired drill cuttings data 214, as well as other data, in an associated database 218.

The device 202 may comprise any device, machine, or apparatus that is able to monitor the drill cuttings 210 such that the cuttings size distribution or density of the drill cuttings 210 may be determined. In some embodiments, for example, the device 202 may comprise a high-speed camera capable of capturing images and/or video of the drill cuttings 210 in real-time or at timed intervals dependent upon the drilling operation (e.g., drilling, circulating, cleaning, etc.). The device 202, for instance, may comprise one or more charge coupled device (CCD) cameras, one or more low light or infrared cameras, a 3D laser scanner, a conoscopic holography camera, a coherent laser radar, one or more touch probes, a magnetic position tracker, or any combination thereof. In at least one embodiment, the device 202 may comprise a high-speed microscope, such as the VW-9000 series microscope available from Keyence of Itasca, Ill., USA. As a camera, the device 202 may be configured to be used in conjunction with one or more light sources 220, such as a white light source, an incandescent light source (e.g., a tungsten filament light bulb), an infrared light source, a laser, one or more light emitting diodes (LEDs), or any combination thereof.

Using a laser as the light source 220 may prove advantageous in allowing an operator to illuminate the drill cuttings 210 with a known wavelength of electromagnetic radiation. As a result, the drilling fluid 122 (FIG. 1) and various additives suspended therein (e.g., lost circulation materials, etc.) may become relatively transparent in contrast to the adjacent drill cuttings 210 such that only the drill cuttings 210 are visible to the device 202 for image capture. In some embodiments, one or more energy modification devices (not shown), such as a polarizer, a beam splitter, and/or a filter may interpose the drill cuttings 210 and the device 202 to reduce the number or breadth of wavelengths seen by the device 202. For instance, a polarizer can be used to align light energy in either the 'P' or 'S' directions (so that the processed energy is p-polarized, or s-polarized), or to generate a blend of P and S polarized energy. A beam splitter may be used to reduce the spectrum of the received energy to some selected or preferred range of wavelengths. Lastly, a filter may be used to further narrow the range to a select spectrum prior to image detection.

In exemplary operation of the device 202 as a camera, the light source(s) 220 may be configured to illuminate the drill cuttings 210 deposited on the shakers 212 and, more particularly, on one or more shaker screens 222 atop which the drill cuttings 210 traverse. The electromagnetic radiation provided by the light source(s) 220 may intensify the images captured by the device 202. The device 202 may be focused on the shaker screens 222 (or a predetermined focal plane offset from the shaker screens 222) to capture images of the drill cuttings 210 as they move across the shaker screens 222. After electromagnetic energy emitted by the drill cuttings 210 is processed by or through the energy modification devices (if present), the device 202 may then receive the electromagnetic energy and transmit the drill cuttings data 214 of the drill cuttings 210 to the data acquisition system 204 for processing.

Processing the drill cuttings data 214 may result in the determination of various characteristics of the drill cuttings 210, such as cuttings size distribution or density of the drill cuttings 210 traversing the shaker screens 222. As used herein, the "density" of the drill cuttings 210 refers to the amount of drill cuttings 210 flowing through the shaker 212 over a certain time period or, in other words, flow rate of the drill cuttings 210. Upon receiving the image data derived from the device 202, a software program stored in the memory 216 (e.g., the database 218) may be programmed with instructions that, when executed by the processor(s) 206, perform desired measurements or analysis on the drill cuttings data 214 to determine cuttings size distribution and/or density of the drill cuttings 210. In at least one embodiment, the software may comprise a three-dimensional (3D) face recognition program or particle size analysis program to measure and determine the desired characteristics of the drill cuttings 210. The live data can be analyzed in real-time by the software to determine the real-time cuttings size distribution and/or density of the drill cuttings 210 traversing the shaker screens 222.

In other embodiments, the device 202 may comprise one or more motion or proximity detectors, such as a capacitive displacement sensor, an inductive sensor, an electromagnetic field sensor, a photoelectric sensor, a through-beam sensor, laser, a retro-reflective sensor, a diffuse sensor, an ultrasonic sensor, and any combination thereof. In such embodiments, the device 202 may be positioned relative to the shaker screen(s) 222 so that any relative motion or movement on top of any of the shaker screens 222 may be detected and reported to the data acquisition system 204 as drill cuttings data 214 for processing. Again, processing the drill cuttings data 214 may result in the determination of at least one of cuttings size distribution and density of the drill cuttings 210 traversing the shaker screens 222.

If the proximity sensor indicates a clear line of sight to the shaker screens 222, that may be an indication that no drill cuttings 210 are currently traversing the shaker screens 222, which may equate to a cuttings size distribution or density of zero. In at least one embodiment, the device 202 as a proximity sensor may be positioned such that its line of sight is parallel to one of the shaker screens 222 and configured to monitor the drill cuttings 210 at one or more predetermined or known heights above the top surface of the shaker screens 222. In such embodiments, the device 202 may be configured to measure and otherwise detect the depth or height of the drill cuttings 210 traversing the shaker screens 222, which may be equated to cuttings size distribution and/or density of the drill cuttings 210. Intelligent proximity sensors, for instance, may be configured to not only detect motion of the drill cuttings 210, but may also be configured to back-calculate the size (e.g., height) of the drill cuttings 210 penetrating the field of detection. For example, a system consisting of three linear motion detectors can duplicate a 3D profile of incoming drill cuttings 210 on the shaker screen 222 for the whole width of the shaker screen 222 and thereby effectively creating a "scanning window."

In yet other embodiments, the device 202 may comprise one or more acoustic sensors. Acoustic sensors operate based on emitting an acoustic signal in certain direction(s) and, based on the travel time back to the source (the speed of sound is known), the exact distance to the source may be calculated, which may be equated to cuttings size distribution and/or density of the drill cuttings 210. Furthermore, an acoustic sensor can travel along a single axis, at set speeds (properly correlated with the speed of moving drill cuttings 210 across the shaker screen 222, speed of processing data, etc.) and can thereby define the one-dimensional profile of the drill cuttings 210. If undertaken concomitantly, two additional, similar sensors mounted orthogonally at a right angle from each other may be coupled and a 3D profile of the drill cuttings 210 can simultaneously be rendered.

In some embodiments, the data acquisition system 204 may comprise and otherwise form part of a remote workstation 224. In other embodiments, the data acquisition system 204 may be configured to communicate with the remote workstation 224 via a transmitter 226, which may include any form of wired or wireless telecommunication such as, but not limited to, wires, fiber optics, or wireless means (e.g., radio frequency, etc.). In such embodiments, the drill cuttings data 214 may be transmitted to the remote workstation 224 to be processed with associated processors 206.

The data acquisition system 204 and/or the remote workstation 224 may include one or more peripheral devices 228, such as a computer screen, a graphical user interface, a hand-held device, a printer, or any combination thereof. The peripheral devices 228 may provide an operator with a graphical display of the results of processing the drill cuttings data 214. Accordingly, the operator may be apprised in real-time of the cuttings size distribution and/or density of the drill cuttings 210 traversing the shaker screens 222. Upon being apprised of cuttings size distribution and/or density of the drill cuttings 210 that fall outside of a predetermined operational threshold, the operator may then have the option of modifying and otherwise altering one or more operational parameters of the shaker 212 to thereby optimize its operation.

More particularly, as mentioned above, one or more operating parameters of the shaker(s) 212 may be modified to ensure that the solids control equipment 128 is operating within a predetermined operating threshold. In some embodiments, the peripheral devices 228 may alert an operator to a cuttings size distribution and/or density of the drill cuttings 210 traversing the shaker screens 222 that falls outside of the predetermined operating threshold. In such embodiments, the operator may decide to proactively adjust and otherwise alter one or more operating parameters of the shaker(s) 212 to optimize their operation. In other embodiments, however, as mentioned above, the system 136 may include an automated control system 230 communicably coupled to the solids control equipment 128 and configured to autonomously adjust the one or more operating parameters. More particularly, when the processed drill cuttings data 214 indicate that the drill cuttings 210 traversing the shaker screens 222 have surpassed a predetermined operational threshold for the drilling fluid 122 (FIG. 1), the automated control system 230 may be activated or otherwise triggered by the data acquisition system 204 to autonomously adjust the one or more operating parameters and thereby bring the solids control equipment 128 back to suitable operational limits.

Figure 3:
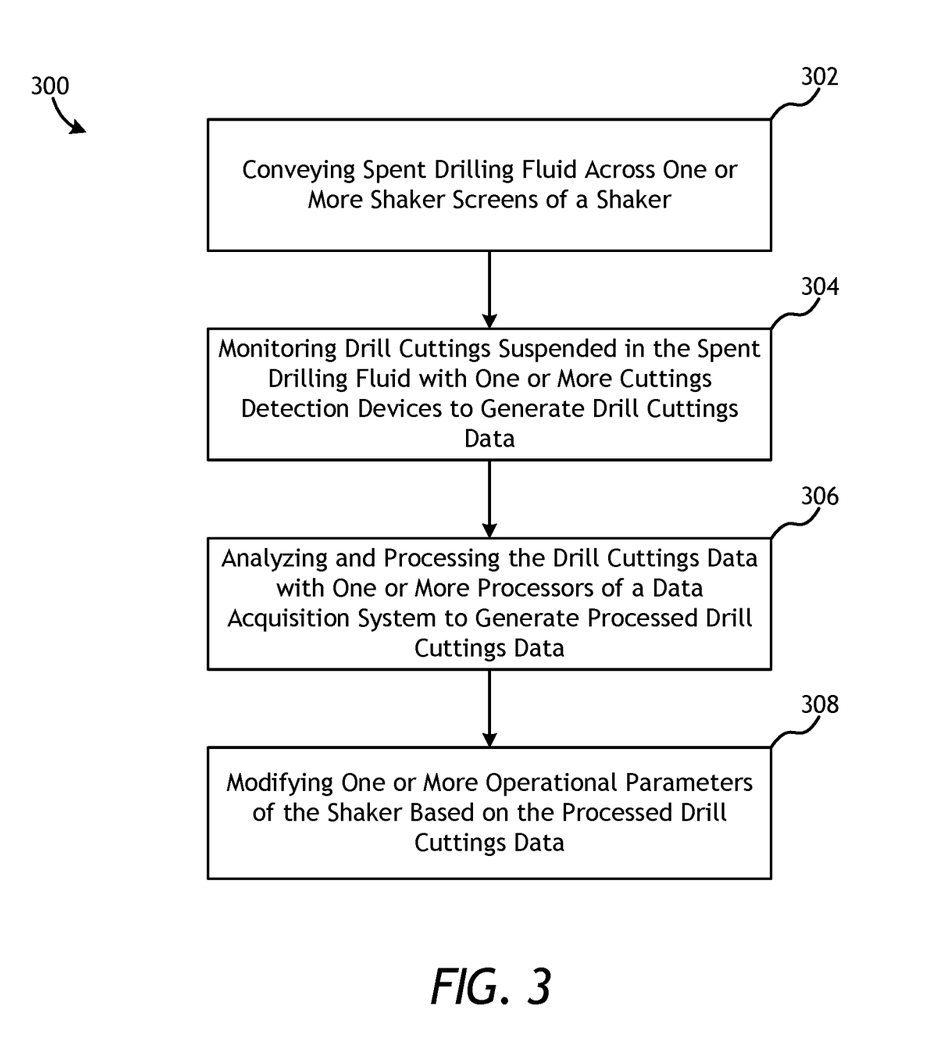
FIG. 3 is a schematic flowchart of an exemplary method in accordance with the principles of the present disclosure.

Referring now to FIG. 3, with continued reference to the prior figures, illustrated is a schematic flowchart of an exemplary method 300, according to one or more embodiments of the present disclosure. Some or all of the steps or parts of the method 300 may be implemented using the imaging system 136 of FIG. 2 in conjunction with the drilling system 100 of FIG. 1. According to the method 300, spent drilling fluid 122 may be conveyed across one or more shaker screens 222 of a shaker 212, as at 302. The shaker 212 may form part of the solids control equipment 128, and the spent drilling fluid 122 may originate from the borehole 116 (e.g., any wellbore) and may include drill cuttings 210 and other particulate material suspended therein.

The drill cuttings 210 may be monitored as they traverse the shaker screens 222 using one or more cuttings detection devices 202, and thereby generating drill cuttings data 214, as at 302. In some embodiments, the cuttings detection device 202 may comprise a camera configured to capture real-time images of the drill cuttings 210 and transmit the drill cuttings data 214 in the form of image data. In other embodiments, the cuttings detection device 202 may comprise one or more motion or proximity sensors configured to detect relative motion of the drill cuttings 210 traversing the shaker screens 222. In yet other embodiments, the cuttings detection device 202 may comprise one or more acoustic sensors.

The drill cuttings data 214 may then be analyzed and processed using one or more processors 206 included in a data acquisition system 204, thereby generating processed drill cuttings data, as at 306. The processed drill cuttings data may be indicative of at least one of a cuttings size distribution and a density of the drill cuttings 210 traversing the shaker screens 222. Once the processed drill cuttings data is obtained, one or more operational parameters of the shaker 210 may be modified, if needed, based on the processed drill cuttings data, as at 308. Modifying the operating parameters of the shakers 210 may bring the shaker 210 back to suitable operational limits. As indicated above, exemplary operating parameters that may be adjusted may include increasing or decreasing an inclination angle (i.e., slope) of the shaker screen 222, increasing or decreasing a vibration amplitude of the shaker 212, increasing or decreasing a vibration frequency of the shaker 212, altering the size (i.e., mesh size) of the shaker screen 222, altering a configuration or mesh profile (e.g., alternative hole shapes) of the shaker screen 222, and any combination thereof.

In some embodiments, for instance, the spent drilling fluid 122 may be conveyed to the shaker 212 at a flow rate that is higher than expected. As a result, the drill cuttings 210 may start to accumulate across the shaker screens 222, which may increase the cuttings size distribution and/or the density of the drill cuttings 210 and result in poor separation of waste from reusable particulates or materials. The accumulation of the drill cuttings 210 may be detected with the cuttings detection devices 202 and result in processed drill cuttings data that exceed a predetermined threshold of suitable operation.

Upon recognizing that the processed drill cuttings data have exceeded the predetermined threshold of suitable operation, the angle of the shaker screen 222 with respect to horizontal may be tilted to ensure that the drill cuttings 210 are properly processed prior to entering the next step of processing. More particularly, an operator or the automated control system 230 may tilt the angle of the shaker screen 222 from about 45° from horizontal, for example, to 55° or more from horizontal, and thereby allow the drill cuttings 210 to traverse the shaker screen 222 more quickly in response to the increased flow rate. Alternatively, if the flow rate of the spent drilling fluid 122 conveyed to the shaker 212 slows, the angle of the shaker screen 222 may be decreased to allow proper cleaning of the drill cuttings 210.

In other embodiments, the processed drill cuttings data may indicate that large clumps or masses of debris or other materials are included in the drill cuttings 210 traversing the shaker screen 222. In such embodiments, an operator or the automated control system 230 may increase the vibration frequency of the shaker 212, which may serve to break apart the clumped debris so that it may be properly screened on the shaker 212. The shaker 212 may include a motor that powers a cam system that provides vibration to the shaker screen 222. Increasing the power output of the motor may correspondingly increase operation of the cam system, and thereby increase the vibration frequency provided by the shaker 212. In some cases, for instance, the vibration frequency may be increased from about 10 Hz to about 20 Hz or higher (e.g., 50 Hz), which may translate into an increased ability to break apart clumped masses of debris or materials on the shaker screens 222.

In yet other embodiments, the processed drill cuttings data may indicate that the shaker 212 is not properly cleaning the drill cuttings 210 and instead passing undesired materials and drill cuttings 210 or otherwise clogging the shaker screens 222. In such embodiments, the shaker 212 may include a plurality of stacked shaker screens 222 and an operator or the automated control system 230 may selectively remove or change out one or more shaker screens 222 to remedy the problem. In some cases, for instance, one or more shaker screens 222 may be removed from the shaker 212. In other cases, however, one or more of the shaker screens 222 may be replaced with shaker screens 222 that have a different mesh size or mesh profile. As will be appreciated, this may prove advantageous in optimizing the shaker 212 with suitable or proper shaker screens 222 for the drill cuttings 210 at any given moment in time, as detected via the imaging system 136.

As will be appreciated, the imaging system 136 may prove advantageous in alerting an operator to the need for different mesh size shaker screens 222. For instance, when drilling through clays or sandstones, different mesh size shaker screens 222 may be required to properly separate the drill cuttings 210 from the spent drilling fluid 122. When the processed drill cuttings data indicate that the shaker 212 is not properly cleaning the drill cuttings 210 and instead passing undesired materials and drill cuttings 210 or otherwise clogging the shaker screens 222, this may be an indication that the drilling has entered a new substrate of a different material. The processed drill cuttings data may alert an operator (or trigger the automated system 230) that a change in mesh size of the shaker screens 222 may be required to return to efficient shaker 212 operation.

Referring again to FIG. 2, the data acquisition system 204 may be generally characterized as a computer or computer system and the computer hardware associated with the data acquisition system 204, such as the processor(s) 206, may be used to implement the various methods and algorithms described herein. More particularly, the processor(s) 206 may be configured to execute one or more sequences of instructions, programming stances, or code stored on a non-transitory, computer-readable medium, such as the memory 216. The processor 206 can be, for example, a general purpose microprocessor, a microcontroller, a digital signal processor, an application specific integrated circuit, a field programmable gate array, a programmable logic device, a controller, a state machine, a gated logic, discrete hardware components, an artificial neural network, or any like suitable entity that can perform calculations or other manipulations of data. The memory 216 may comprise at least one of random access memory (RAM), flash memory, read only memory (ROM), programmable read only memory (PROM), and electrically erasable programmable read only memory (EEPROM). The memory 216 may further include one or more of registers, hard disks, removable disks, CD-ROMS, DVDs, or any other like suitable storage device or medium.

Executable sequences described herein can be implemented with one or more sequences of code contained in the memory 216. In some embodiments, such code can be read into the memory 216 from another machine-readable medium. Execution of the sequences of instructions contained in the memory can cause the processor 206 to perform the process steps described herein. As will be appreciated, one or more processors 104 in a multi-processing arrangement can also be employed to execute instruction sequences in the memory 216. In addition, hard-wired circuitry can be used in place of or in combination with software instructions to implement various embodiments described herein. Thus, the present embodiments are not limited to any specific combination of hardware and/or software.

Embodiments disclosed herein include:

A. A method that includes monitoring drill cuttings suspended within a drilling fluid with one or more cuttings detection devices as the drill cuttings traverse one or more shaker screens of a shaker, generating drill cuttings data of the drill cuttings with the one or more cuttings detection devices, analyzing and processing the drill cuttings data with one or more processors included in a data acquisition system and thereby generating processed drill cuttings data, wherein the processed drill cuttings data is indicative of at least one of a cuttings size distribution and a density of the drill cuttings, and modifying one or more operational parameters of the shaker based on the processed drill cuttings data.

B. A method of drilling a wellbore that includes rotating a drill bit positioned at an end of a drill string extended into a borehole from a surface location, circulating drilling fluid through the drill string and back to the surface location, receiving spent drilling fluid having drill cuttings suspended therein at a shaker, monitoring the drill cuttings with one or more cuttings detection devices as the drill cuttings traverse one or more shaker screens of the shaker, and thereby generating drill cuttings data, analyzing and processing the drill cuttings data with one or more processors included in a data acquisition system and thereby generating processed drill cuttings data, wherein the processed drill cuttings data is indicative of at least one of a cuttings size distribution and a density of the drill cuttings, and modifying one or more operational parameters of the shaker based on the processed drill cuttings data.

Each of embodiments A and B may have one or more of the following additional elements in any combination: Element 1: wherein the one or more cuttings detection devices comprises a camera, and wherein monitoring the drill cuttings with the one or more cuttings detection devices comprises capturing images of the drill cuttings with the camera and thereby generating image data, and receiving the image data with the data acquisition system. Element 2: wherein the camera is a high-speed camera selected from the group consisting of a charge coupled device camera, a low light camera, an infrared camera, and a high-speed microscope. 3D laser scanner, conoscopic holography, coherent laser radar, touch probes, magnetic position trackers. Element 3: wherein the one or more cuttings detection devices comprise one or more motion sensors, and wherein monitoring the drill cuttings with the one or more cuttings detection devices comprises detecting relative motion of the drill cuttings with the one or more motion sensors as the drill cuttings traverse the one or more shaker screens. Element 4: wherein detecting the relative motion of the drill cuttings comprises monitoring the drill cuttings at a known height above a surface of the one or more shaker screens, and determining a depth of the drill cuttings traversing the one or more shaker screens based on a height measurement of the drill cuttings traversing the one or more shaker screens. Element 5: wherein the one or more cuttings detection devices comprise one or more acoustic sensors and wherein monitoring the drill cuttings with the one or more cuttings detection devices comprises emitting an acoustic signal with the one or more acoustic sensors toward the drill cuttings, and determining a distance between the one or more acoustic sensors and the drill cuttings based on a travel time required for the acoustic signal to return to the one or more acoustic sensors. Element 6: wherein modifying the one or more operational parameters of the shaker comprises manually altering the one or more operational parameters. Element 7: wherein modifying the one or more operational parameters of the shaker comprises altering the one or more operational parameters with an automated control system communicably coupled to the shaker. Element 8: wherein modifying the one or more operational parameters of the shaker comprises increasing or decreasing an inclination angle of at least one of the one or more shaker screens. Element 9: wherein modifying the one or more operational parameters of the shaker comprises increasing or decreasing at least one of a vibration frequency and a vibration amplitude of the shaker. Element 10: wherein modifying the one or more operational parameters of the shaker comprises altering at least one of a mesh size and a mesh profile of at least one of the one or more shaker screens. Element 11: wherein modifying the one or more operational parameters of the shaker comprises removing at least one of the one or more shaker screens. Element 12: wherein modifying the one or more operational parameters of the shaker comprises replacing at least one of the one or more shaker screens with a shaker screen of a different mesh size or mesh profile.

Element 13: wherein the one or more cuttings detection devices comprises a camera, and wherein monitoring the drill cuttings with the one or more cuttings detection devices comprises capturing images of the drill cuttings with the camera and thereby generating image data, and receiving the image data with the data acquisition system. Element 14: wherein the one or more cuttings detection devices comprise one or more motion sensors, and wherein monitoring the drill cuttings with the one or more cuttings detection devices comprises detecting relative motion of the drill cuttings with the one or more motion sensors as the drill cuttings traverse the one or more shaker screens. Element 15: wherein the one or more cuttings detection devices comprise one or more acoustic sensors and wherein monitoring the drill cuttings with the one or more cuttings detection devices comprises emitting an acoustic signal with the one or more acoustic sensors toward the drill cuttings, and determining a distance between the one or more acoustic sensors and the drill cuttings based on a travel time required for the acoustic signal to return to the one or more acoustic sensors. Element 16: wherein modifying the one or more operational parameters of the shaker comprises increasing or decreasing an inclination angle of at least one of the one or more shaker screens. Element 17: wherein modifying the one or more operational parameters of the shaker comprises increasing or decreasing at least one of a vibration frequency and a vibration amplitude of the shaker. Element 18: wherein modifying the one or more operational parameters of the shaker comprises altering at least one of a mesh size and a mesh profile of at least one of the one or more shaker screens. Element 19: wherein modifying the one or more operational parameters of the shaker comprises removing at least one of the one or more shaker screens. Element 20: wherein modifying the one or more operational parameters of the shaker comprises replacing at least one of the one or more shaker screens with a shaker screen of a different mesh size or mesh profile.

By way of non-limiting example, exemplary combinations applicable to A and B include: Element 1 with Element 2; and Element 3 with Element 4.

Therefore, the disclosed systems and methods are well adapted to attain the ends and advantages mentioned as well as those that are inherent therein. The particular embodiments disclosed above are illustrative only, as the teachings of the present disclosure may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered, combined, or modified and all such variations are considered within the scope of the present disclosure. The systems and methods illustratively disclosed herein may suitably be practiced in the absence of any element that is not specifically disclosed herein and/or any optional element disclosed herein. While compositions and methods are described in terms of "comprising," "containing," or "including" various components or steps, the compositions and methods can also "consist essentially of" or "consist of" the various components and steps. All numbers and ranges disclosed above may vary by some amount. Whenever a numerical range with a lower limit and an upper limit is disclosed, any number and any included range falling within the range is specifically disclosed. In particular, every range of values (of the form, "from about a to about b," or, equivalently, "from approximately a to b," or, equivalently, "from approximately a-b") disclosed herein is to be understood to set forth every number and range encompassed within the broader range of values. Also, the terms in the claims have their plain, ordinary meaning unless otherwise explicitly and clearly defined by the patentee. Moreover, the indefinite articles "a" or "an," as used in the claims, are defined herein to mean one or more than one of the elements that it introduces. If there is any conflict in the usages of a word or term in this specification and one or more patent or other documents that may be incorporated herein by reference, the definitions that are consistent with this specification should be adopted.

As used herein, the phrase "at least one of" preceding a series of items, with the terms "and" or "or" to separate any of the items, modifies the list as a whole, rather than each member of the list (i.e., each item). The phrase "at least one of" allows a meaning that includes at least one of any one of the items, and/or at least one of any combination of the items, and/or at least one of each of the items. By way of example, the phrases "at least one of A, B, and C" or "at least one of A, B, or C" each refer to only A, only B, or only C; any combination of A, B, and C; and/or at least one of each of A, B, and C.

What is claimed is:

1. A method, comprising:
   shining a laser light source on one or more drill cuttings suspended within a drilling fluid wherein the drill cuttings traverse one or more shaker screens of a shaker;
   capturing reflected laser light using one or more cuttings detection devices comprising a microscope positioned above the one or more shaker screens;
   generating drill cuttings data of the drill cuttings with the one or more cuttings detection devices;
   analyzing and processing the drill cuttings data with one or more processors included in a data acquisition system and thereby generating processed drill cuttings data, wherein the processed drill cuttings data is indicative of at least one of a cuttings size distribution or a density of the drill cuttings; and
   modifying one or more operational parameters of the shaker based on at least one of the cuttings size distribution or the density of the drill cuttings.

2. The method of claim 1, wherein the one or more cuttings detection devices further comprises a camera, and wherein monitoring the drill cuttings with the one or more cuttings detection devices comprises:
   capturing images of the drill cuttings with the camera and thereby generating image data; and
   receiving the image data with the data acquisition system.

3. The method of claim 1, wherein the one or more cuttings detection devices further comprises conoscopic holography, coherent laser radar, touch probes, or magnetic position trackers.

4. The method of claim 1, wherein the one or more cuttings detection devices comprise one or more motion sensors, and wherein monitoring the drill cuttings with the one or more cuttings detection devices comprises detecting relative motion of the drill cuttings with the one or more motion sensors as the drill cuttings traverse the one or more shaker screens.

5. The method of claim 4, wherein detecting the relative motion of the drill cuttings comprises:
   monitoring the drill cuttings at a known height above a surface of the one or more shaker screens; and determining a depth of the drill cuttings traversing the one or more shaker screens based on a height measurement of the drill cuttings traversing the one or more shaker screens.

6. The method of claim 1, wherein the one or more cuttings detection devices comprise one or more acoustic sensors and wherein monitoring the drill cuttings with the one or more cuttings detection devices comprises:
emitting an acoustic signal with the one or more acoustic sensors toward the drill cuttings; and
determining a distance between the one or more acoustic sensors and the drill cuttings based on a travel time required for the acoustic signal to return to the one or more acoustic sensors.

7. The method of claim 1, wherein modifying the one or more operational parameters of the shaker comprises manually altering the one or more operational parameters.

8. The method of claim 1, wherein modifying the one or more operational parameters of the shaker comprises altering the one or more operational parameters with an automated control system communicably coupled to the shaker.

9. The method of claim 1, wherein modifying the one or more operational parameters of the shaker comprises increasing or decreasing an inclination angle of at least one of the one or more shaker screens.

10. The method of claim 1, wherein modifying the one or more operational parameters of the shaker comprises increasing or decreasing at least one of a vibration frequency or a vibration amplitude of the shaker.

11. The method of claim 1, wherein modifying the one or more operational parameters of the shaker comprises altering at least one of a mesh size or a mesh profile of at least one of the one or more shaker screens.

12. The method of claim 1, wherein modifying the one or more operational parameters of the shaker comprises removing at least one of the one or more shaker screens.

13. The method of claim 1, wherein modifying the one or more operational parameters of the shaker comprises replacing at least one of the one or more shaker screens with a shaker screen of a different mesh size or mesh profile.

14. A method of drilling a wellbore, comprising:
rotating a drill bit positioned at an end of a drill string extended into a borehole from a surface location;
circulating drilling fluid through the drill string and back to the surface location;
receiving spent drilling fluid having drill cuttings suspended therein at a shaker;
monitoring the drill cuttings with one or more cuttings detection devices as the drill cuttings traverse one or more shaker screens of the shaker, and thereby generating drill cuttings data, wherein the one of more cuttings detection devices comprise three or more linear motion detectors and a microscope positioned above the one or more shaker screens;
analyzing and processing the drill cuttings data with one or more processors included in a data acquisition system and thereby generating processed drill cuttings data comprising a 3D profile of the drill cuttings and determining a height of the drill cuttings, wherein the height of the drill cuttings is indicative of at least one of a cuttings size distribution or a density of the drill cuttings; and
modifying one or more operational parameters of the shaker based on the cuttings size distribution or the density of the drill cuttings.

15. The method of claim 14, wherein the one or more cuttings detection devices further comprises a camera, and wherein monitoring the drill cuttings with the one or more cuttings detection devices further comprises:
capturing images of the drill cuttings with the camera and thereby generating image data; and
receiving the image data with the data acquisition system.

16. The method of claim 14, wherein the one or more cuttings detection devices further comprise one or more acoustic sensors and wherein monitoring the drill cuttings with the one or more cuttings detection devices comprises:
emitting an acoustic signal with the one or more acoustic sensors toward the drill cuttings; and
determining a distance between the one or more acoustic sensors and the drill cuttings based on a travel time required for the acoustic signal to return to the one or more acoustic sensors.

17. The method of claim 14, wherein modifying the one or more operational parameters of the shaker comprises increasing or decreasing an inclination angle of at least one of the one or more shaker screens.

18. The method of claim 14, wherein modifying the one or more operational parameters of the shaker comprises increasing or decreasing at least one of a vibration frequency or a vibration amplitude of the shaker.

19. The method of claim 14, wherein modifying the one or more operational parameters of the shaker comprises altering at least one of a mesh size or a mesh profile of at least one of the one or more shaker screens.

20. The method of claim 14, wherein modifying the one or more operational parameters of the shaker comprises removing at least one of the one or more shaker screens.

21. The method of claim 14, wherein modifying the one or more operational parameters of the shaker comprises replacing at least one of the one or more shaker screens with a shaker screen of a different mesh size or mesh profile.

* * * * *